US00PP13229P2

(12) United States Plant Patent
Hammett

(10) Patent No.: US PP13,229 P2
(45) Date of Patent: Nov. 12, 2002

(54) NEMESIA PLANT NAMED 'NEMLI'

(75) Inventor: Keith Richard William Hammett, Auckland (NZ)

(73) Assignee: Seaview Nurseries Ltd., Manurewa (NZ)

( * ) Notice: Subject to any disclaimer, the term of this patent is extended or adjusted under 35 U.S.C. 154(b) by 0 days.

(21) Appl. No.: 09/968,327

(22) Filed: Sep. 30, 2001

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,014 P2 * 7/2001 Hubbard ..... Plt./263

* cited by examiner

*Primary Examiner*—Kent L. Bell
(74) *Attorney, Agent, or Firm*—C. A. Whealy

(57) ABSTRACT

A new and distinct cultivar of Nemesia plant named 'Nemli', characterized by its upright, outwardly spreading and compact plant habit; freely branching habit; small green leaves; and numerous light purple-colored flowers.

1 Drawing Sheet

BOTANICAL CLASSIFICATION/CULTIVAR DESIGNATION

*Nemesia caerula* cultivar 'Nemli'.

BACKGROUND OF THE INVENTION

The present invention relates to a new and distinct cultivar of Nemesia plant, botanically known as *Nemesia caerula* and referred to by the name 'Nemli'.

The new Nemesia is a product of a planned breeding program conducted by the Inventor in Auckland, New Zealand. The objecive of the program is to create new compact Nemesia cultivars with numerous flowers and unique flower colors.

The new Nemesia originated from a cross by the Inventor of the *Nemesia caerula* cultivar 'Pearl', not patented, as the female, or seed, parent with the *Nemesia caerula* cultivar 'Delphi', not patented, as the male, or pollen, parent on or about Oct. 30, 1998. The cultivar 'Nemli' was discovered and selected by the Inventor as a flowering plant within the progeny of the stated cross in a controlled environment in Auckland, New Zealand on or about Apr. 16, 1999.

Asexual reproduction of the new Nemesia by terminal cuttings taken in a controlled environment in Auckland, New Zealand since April, 1999, has shown that the unique features of this new Nemesia are stable and are reproduced true to type in successive generations.

SUMMARY OF THE INVENTION

The new Nemesia has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Nemli' and distinguish 'Nemli' as a new and distinct cultivar:

1. Upright, outwardly spreading and compact plant habit.
2. Freely branching habit.

3. Small green leaves.
4. Numerous light purple-colored flowers.

Plants of the new Nemesia differ primarily from plants of the female parent, the cultivar 'Pearl', in the following characteristics:

1. Plants of the the new Nemesia are more compact than plants of the cultivar 'Pearl'.
2. Plants of the new Nemesia are more freely flowering than plants of the cultivar 'Pearl'.
3. Plants of the new Nemesia have light purple-colored flowers whereas plants of the cultivar 'Pearl' have pale pink-colored flowers.

Plants of the new Nemesia differ primarily from plants of the male parent, the cultivar 'Delphi', in flower color.

Plants of the new Nemesia can be compared to plants of the cultivar 'Blueberry Sachet', not patented. In side-by-side comparisons conducted in Encinitas, Calif., plants of the new Nemesia differed from plants of the cultivar 'Blueberry Sachet' in the following characteristics:

1. Plants of the new Nemesia were larger and more outwardly spreading than plants of the cultivar 'Blueberry Sachet'.
2. Plants of the new Nemesia had lighter green foliage than plants of the cultivar 'Blueberry Sachet'.
3. Plants of the new Nemesia had light purple-colored flowers whereas plants of the cultivar 'Blueberry Sachet' had blue-colored flowers.

BRIEF DESCRIPTION OF THE PHOTOGRAPHS

The accompanying colored photographs illustrate the overall apperance of the new Nemesia, showing the colors as true as it is reasonably possible to obtain in colored reproductions of this type. Colors in the photographs may differ slightly from the color values cited in the detailed botanical description which accurately describe the colors of the new Nemesia.

The photograph at the top of the sheet comprises a side perspective view of a typical potted plant of 'Nemli' that was about 14 weeks old.

The photograph at the bottom of the sheet comprises a close-up view of typical leaves and flowers of 'Nemli'.

DETAILED BOTANICAL DESCRIPTION

The aforementioned photographs and following observations and averaged measurements describe plants grown in Encinitas, Calif., in a polyethylene-covered greenhouse during the spring with day temperatures about 24° C., night temperatures about 19° C., and light levels about 4,000 foot-candles. Plants were grown for 14 weeks in 16.5-cm containers with one plant per container and were pinched. Color references are made to The Royal Horticultural Society Colour Chart except where general terms of ordinary dictionary significance are used.

Parentage:

*Female parent.*—*Nemesia caerula* cultivar 'Pearl', not patented.

*Male parent.*—*Nemesia caerula* cultivar 'Delphi', not patented.

Propagation:

*Type.*—By vegetative cuttings.

*Time to initiate roots.*—About 14 days at 20° C.

*Time to develop roots.*—About 30 days at 20° C.

*Root description.*—Fibrous, fine.

Plant description:

*General appearance.*—Upright, outwardly spreding and compact plant habit. Freely branching, typically about 30 laterals with numerous secondary laterals developing after pinching. Numerous light purple-colored zygomorphic flowers. Moderately vigorous.

*Plant height.*—About 28 cm.

*Plant diameter or spread.*—About 40 cm.

*Lateral branches.*—Appearance: Slender and filamentous; square in cross-section. Length: About 26 cm. Diameter: About 3 mm. Internode length: About 2.5 to 6 cm. Strength: Moderately strong, wiry; with development, lateral branches tend to bend with weight of flowers. Texture: Glabrous. Color: 144A.

*Foliage description.*—Arrangement: Opposite, simple. Quantity: About 12 to 14 per lateral branch. Shape: Elliptic. Apex: Broadly acute. Base: Acute to rounded. Length: About 3 cm. Width: About 1.8 cm. Margin: Serrate. Texture: Glabrous. Venation pattern: Pinnate, arcuate. Frgrance: Pungent, grassy. Petiole length: About 5 mm. Petiole diameter: About 2 mm. Color: Young leaves, upper surface: 147A. Young leaves, lower surface: 147B. Fully expanded leaves, upper surface: 147B. Fully expanded leaves, lower surface 147C. Venation, upper surface: 147B. Venation, lower surface: 147C. Petiole: 147B.

Flowering description:

*Arrangement/appearance.*—Zygomorphic solitary flowers arranged on terminal racemes; flowering acropetally towards apex. Flowers bilabiate with nectar spur. Flowers face outward. Flowers last about four to five days on the plant. Flowers not persistent.

*Natural flowering season.*—Natural flowering season is spring to fall; flowering continuous during this period.

*Quantity of flowers.*—Freely flowering with about 15 flowers and flower buds per raceme at one time.

*Fragrance.*—Faint, spicy and sweet.

*Inflorescence length.*—About 11.5 cm.

*Inflorescence diameter.*—About 2 cm.

*Flower length.*—About 1 cm.

*Flower width.*—About 1.5 cm.

*Flower depth, including nectar spur.*—About 1 cm.

*Nectar spur length.*—About 7 mm.

*Flower buds.*—Shape: Ovoid with spur. Length: About 6 mm. Diameter: About 5 mm. Color: 85C to 85D.

*Petals.*—Arrangement/shape: Five petals total. Four upper petals are fused at base to form an upright lobed and arched banner lip; lower petal modified into a larger lip with nectar spur and convex oval protuberance which serves as pollinator nectar guide and landing platform. Apex: Rounded. Margin: Entire. Length: Upper lip petals: About 7 mm. Lower lip petal: About 9 mm. Width: Upper lip petals: Lateral two petals: About 5 mm Center two petals: About 4 mm. Lower lip petal: About 1.2 cm. Texture: Smooth, velvety. Color: When opening, upper surface: 87A. When opening, lower surface: 76B. Fully opened, upper surface: 88C; color fading to 84A towards the margin and 85A towards the center with subsequent development. Fully opened, lower surface: 76C to 76D. Nectar guide: 9B. Nectar spur: 155B.

*Sepals.*—Quantity: Five-parted, star-shaped calyx. Shape: Elliptic. Apex: Acute. Base: Fused. Margin: Entire. Length: About 2 mm. Diameter: About 1.5 mm. Texture, upper and lower surfaces: Pubescent. Color: Upper surface: 144A. Lower surface: 147B.

*Peduncle.*—Length: About 11.5 cm. Diameter: About 1.5 mm. Strength: Strong. Angle: Upright to 45° from the stem. Color: 144C.

*Pedicle.*—Length: About 8 mm. Diameter: Less than 1 mm. Strength: Slender, but hold flowers outward. Angle: About 45° from the stem. Color: 144C.

*Androecium.*—Stamen number: Four per flower. Anther shape: Oval. Anther size: Less than 1 mm. Anther color: 6A. Amount of pollen: Scarce. Pollen color: 6A.

*Gynoecium.*—Pistil number: One per flower. Stigma shape: Flattened. Pistil length: About 2 mm. Style length: About 1 mm. Style color: 144D. Stigma shape: Rounded. Stigma color: 144D. Ovary color: 144B.

*Seed/fruit.*—Seed and fruit production has not been observed on plants of the new Nemesia.

Disease/pest resistance: Plants of the new Nemesia have not been observed to be resistant to pathogens or pests common to Nemesias.

Temperature tolerance: Plants of the new Nemesia have been observed to be tolerant to temperatures ranging from 4° to 32° C.

It is claimed:

1. A new and distinct cultivar of Nemesia plant named 'Nemli', as illustrated and described.

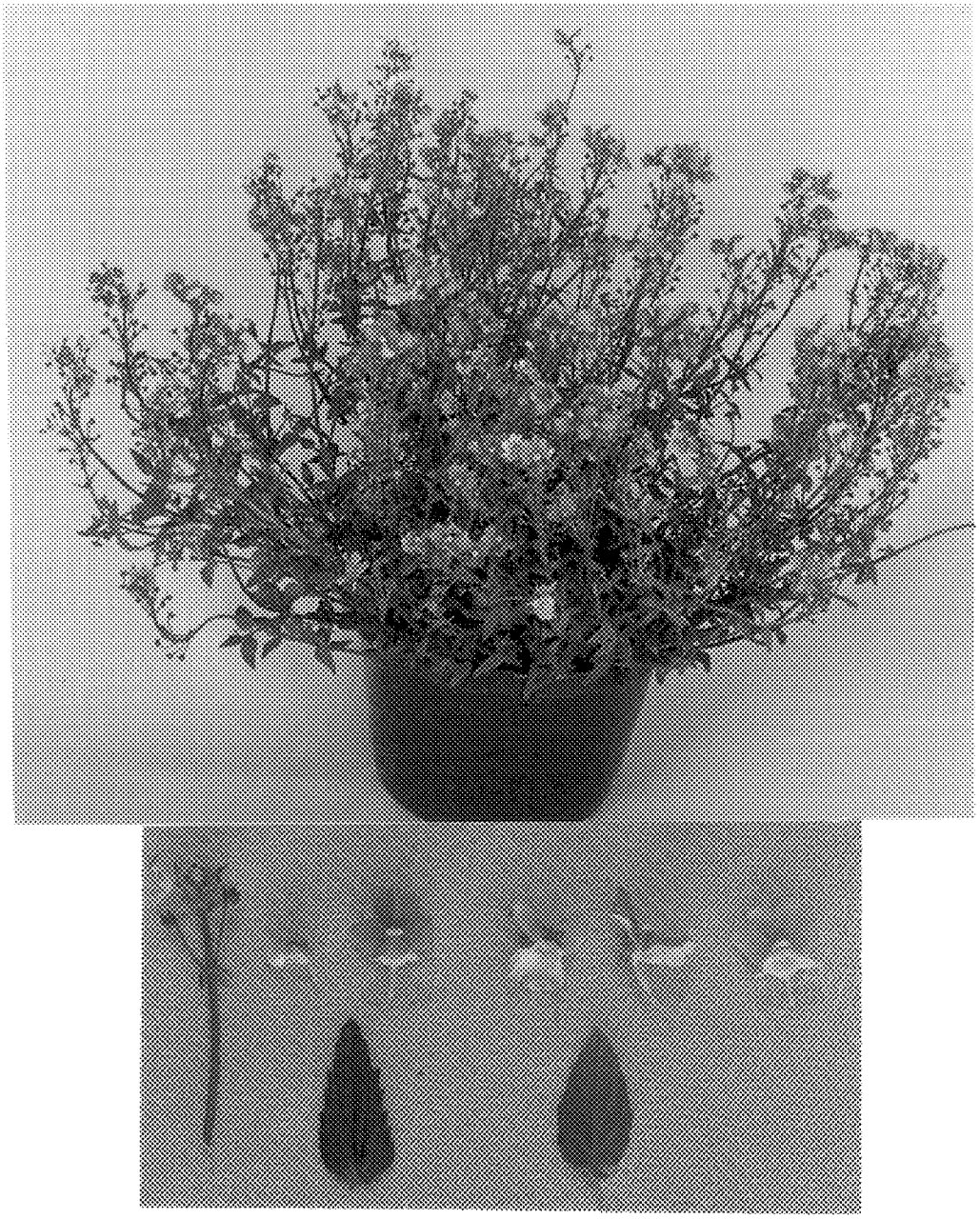

* * * * *